United States Patent [19]

Nelson et al.

[11] Patent Number: 5,824,475

[45] Date of Patent: Oct. 20, 1998

[54] OLIGONUCLEOTIDE SCREENING ASSAY USING DNA-ALTERING AGENTS AND PROBES WITH PROTECTABLE LABELS

[75] Inventors: Norman C. Nelson; Jorge Velarde, Jr.; Daniel L. Kacian, all of San Diego, Calif.

[73] Assignee: Gen-Probe Incorporated, San Diego, Calif.

[21] Appl. No.: 480,884

[22] Filed: Jun. 7, 1995

Related U.S. Application Data

[63] Continuation of Ser. No. 94,577, Jul. 19, 1993, abandoned.

[51] Int. Cl.$^6$ ........................................... C12Q 1/68
[52] U.S. Cl. ............................... 435/6; 436/94; 436/501
[58] Field of Search .......................... 435/6, 810; 436/94, 436/501

[56] References Cited

U.S. PATENT DOCUMENTS

| | | | |
|---|---|---|---|
| 4,683,194 | 7/1987 | Saiki et al. | 435/6 |
| 4,725,537 | 2/1988 | Fritsch et al. | 435/6 |
| 4,876,187 | 10/1989 | Duck et al. | 435/6 |
| 5,011,769 | 4/1991 | Duck et al. | 435/6 |
| 5,030,557 | 7/1991 | Hogan et al. | 435/6 |
| 5,102,784 | 4/1992 | George, Jr. | 435/6 |
| 5,185,439 | 2/1993 | Arnold, Jr. et al. | 536/24.3 |
| 5,283,174 | 2/1994 | Arnold, Jr. et al. | 435/6 |
| 5,317,009 | 5/1994 | Lee-Huang et al. | 514/8 |
| 5,403,711 | 4/1995 | Walder et al. | 435/6 |

FOREIGN PATENT DOCUMENTS

| | | |
|---|---|---|
| 0309230 | 3/1989 | European Pat. Off. . |
| 8902896 | 4/1989 | WIPO . |
| 9207864 | 5/1992 | WIPO . |

OTHER PUBLICATIONS

Nelson et al., *Clin. Chim. Acta* 194, 73–90 (1990).

Arnold, Jr et al., *Clin. Chem.* 35(8), 1588–1594 (1989).

Young et al., *Nucleic Acids Res.* 19(9), 2463–2470 (1991).

Urdea et al., "A comparison of non-radioisotopic hybridization assay methods using fluorescent, chemiluminescent and enzyme labeled synthetic oligodeoxyribonucleotide probes," *Nucleic Acids Research* 16:4937–4956 (1988).

Yehle et al., "A Solution hybridization assay for ribosomal RNA from bacteria using biotinylated DNA probes and enzyme-labeled antibody to DNA:RNA," *Molecular and Cellular Probes* 1:177–193 (1987).

Southern, "Detection of Specific Sequences Among DNA Fragments Separated by Gel Electrophoresis," *J. Mol. Biol.* 98:503–517 (1975).

McSwiggen et al., "Probing RNA Accessibility with RNase H" Abstract, (1991).

(List continued on next page.)

*Primary Examiner*—Kenneth R. Horlick
*Attorney, Agent, or Firm*—Lyon & Lyon LLP

[57] ABSTRACT

The invention features a method for assaying the ability of an oligonucleotide to form a hybrid with a target nucleic acid sequence. The featured assay comprises the following steps: (a) contacting a test sample containing a target nucleic acid sequence with an oligonucleotide; (b) treating the test sample with a duplex-altering agent; (c) contacting the treated test sample with a labeled probe under stringent hybridization conditions, wherein the probe can hybridize to non-altered target nucleic acid sequence such that the probe label is protected from subsequent chemical inactivation but the probe cannot hybridize to altered target nucleic acid sequence in a manner which would protect the probe label from subsequent chemical inactivation; and (d) measuring the hybridization of the probe to non-altered target nucleic acid sequence by measuring the amount of protected label. Also described is an assay to measure the ability of a ribozyme to cleave a target nucleic acid sequence, and an assay to measure the ability of an agent to alter nucleic acid.

31 Claims, 5 Drawing Sheets

OTHER PUBLICATIONS

Uhlmann and Peyman, "Antisense Oligonucleotides: A New Therapeutic Principle," *Chemical Reviews* 90:544–584 (1990).

Lingelback and Dobberstein, "An extended RNA/RNA duplex structure within the coding region of mRNA does not block translational elongation," *Nucleic Acids Research* 16:3405–3414 (1988).

Hélène and Toulmé, "Specific regulation of gene expression by antisense, sence and antigene nucleic acids," *Chemica et Biophysica Acta* 1049:99–125 (1990).

Nelson, "Detection of Acridinium Esters by Chemiluminescence," pp. 275–310, Nonisotopic DNA Probe Techniques, Larry J. Kricka ed., *Academic Press, Inc.* San Diego (1992).

Caruthers et al., "Chemical Synthesis of Deoxyoligonucleotides by the Phosphoramidite Method," *Science* 230:287–313 (1985).

Kotewicz et al., "Isolation of cloned Moloney murine leukemia virus reverse transcriptase lacking ribonuclease H activity," *Nucleic Acids Research* 16:265–277 (1988).

A. Protected Acridinium ester (Acridinium ester denoted by an x).

mRNA    ApGpUpUpCpApGpCpGpGpCpGpCpCpUpUpApUpApUpCpCpGpG
        . . . . . . . . . . . . . x . . . . . . . . .
        . . . . . . . . . . . . .—|—. . . . . . . . .
Probe   TpCpApApGpTpCpGpCpCpGpGpApApTpApGpGpGpCpCpCp B. Less protected Acridinium ester positioned at cut target site.

mRNA    ApGpUpUpCpApGpCpApGpCpgpGpCp
        . . . . . . . . . . . x . .
        . . . . . . . . . . .—|—. .
Probe   TpCpApApGpTpCpGpCpCpGpGpApApTpApGpGpGpCpCpCp C. Unprotected Acridinium ester present on single stranded probe.

x
                                    —|—
Probe   TpCpApApGpTpCpGpCpCpGpGpApApTpApGpGpGpCpCpCp -

FIG. 1

SEQUENCE LISTING ( 1 ) GENERAL INFORMATION:

( i i i ) NUMBER OF SEQUENCES: 10

( 2 ) INFORMATION FOR SEQ ID NO: 1:

( i ) SEQUENCE CHARACTERISTICS:
( A ) LENGTH: 23
( B ) TYPE: nucleic acid
( C ) STRANDEDNESS: single
( D ) TOPOLOGY: linear ( i i ) SEQUENCE DESCRIPTION: SEQ ID NO: 1:

GCACCATTCT GTCTGTTTTG GGG     23

( 2 ) INFORMATION FOR SEQ ID NO: 2:

( i ) SEQUENCE CHARACTERISTICS:
    ( A ) LENGTH: 21
    ( B ) TYPE: nucleic acid
    ( C ) STRANDEDNESS: single
    ( D ) TOPOLOGY: linear ( i i ) SEQUENCE DESCRIPTION: SEQ ID NO: 2:

CCGATCTTTT CCCAGGCAGT C    21

( 2 ) INFORMATION FOR SEQ ID NO: 3:

( i ) SEQUENCE CHARACTERISTICS:
    ( A ) LENGTH: 24
    ( B ) TYPE: nucleic acid
    ( C ) STRANDEDNESS: single
    ( D ) TOPOLOGY: linear ( i i ) SEQUENCE DESCRIPTION: SEQ ID NO: 3:

CCATGGTGGT TCCTTCTCAG TCGG    24

( 2 ) INFORMATION FOR SEQ ID NO: 4:

( i ) SEQUENCE CHARACTERISTICS:
    ( A ) LENGTH: 21
    ( B ) TYPE: nucleic acid
    ( C ) STRANDEDNESS: single
    ( D ) TOPOLOGY: linear ( i i ) SEQUENCE DESCRIPTION: SEQ ID NO: 4:

CCCAAGAACA TCCTCTCCAC G    21

( 2 ) INFORMATION FOR SEQ ID NO: 5:

( i ) SEQUENCE CHARACTERISTICS:
    ( A ) LENGTH: 23
    ( B ) TYPE: nucleic acid
    ( C ) STRANDEDNESS: single
    ( D ) TOPOLOGY: linear ( i i ) SEQUENCE DESCRIPTION: SEQ ID NO: 5:

GCACCATTCT GTCTGTTTTG GGG    23

( 2 ) INFORMATION FOR SEQ ID NO: 6:

( i ) SEQUENCE CHARACTERISTICS:
    ( A ) LENGTH: 21
    ( B ) TYPE: nucleic acid
    ( C ) STRANDEDNESS: single
    ( D ) TOPOLOGY: linear ( i i ) SEQUENCE DESCRIPTION: SEQ ID NO: 6:

CAGGGCCTCA CCACCAACTT C    21

( 2 ) INFORMATION FOR SEQ ID NO: 7:

( i ) SEQUENCE CHARACTERISTICS:
    ( A ) LENGTH: 22
    ( B ) TYPE: nucleic acid
    ( C ) STRANDEDNESS: single
    ( D ) TOPOLOGY: linear ( i i ) SEQUENCE DESCRIPTION: SEQ ID NO: 7:

CAGGTCCCCA AAGGACTCGA AG    22

( 2 ) INFORMATION FOR SEQ ID NO: 8:

( i ) SEQUENCE CHARACTERISTICS:
    ( A ) LENGTH: 52

```
        ( B ) TYPE: nucleic acid
        ( C ) STRANDEDNESS: single
        ( D ) TOPOLOGY: linear ( i i ) SEQUENCE DESCRIPTION: SEQ ID NO: 8:

AATTTAATAC  GACTCACTAT  AGGGAGAGGT                                    3 0

TATCGCTGGA  TGTGTCTGCG  GC                                            5 2

( 2 ) INFORMATION FOR SEQ ID NO: 9:

( i ) SEQUENCE CHARACTERISTICS:
        ( A ) LENGTH: 126
        ( B ) TYPE: nucleic acid
        ( C ) STRANDEDNESS: single
        ( D ) TOPOLOGY: linear ( i i ) SEQUENCE DESCRIPTION: SEQ ID NO: 9:

TCCTGGAATT  AGAGGACAAA  CGGGCAACAT                                    3 0

ACCTTGATAA  TCCAGAAGAA  CCAATAAGAA                                    6 0

GATGAGGCAT  AGCAGCAGGA  TGAAGAGGAA                                    9 0

TATGATAAAA  CGCCGCAGAC  ACATCCAGCG                                    1 2 0

ATAACC                                                                1 2 6

( 2 ) INFORMATION FOR SEQ ID NO: 10:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( i i ) SEQUENCE DESCRIPTION: SEQ ID NO: 10:

GAGGCATAGC  AGCAGGATGA  AGAGG                                         2 5
```

OLIGONUCLEOTIDE SCREENING ASSAY USING DNA-ALTERING AGENTS AND PROBES WITH PROTECTABLE LABELS

This application is a continuation application Ser. No. 08/094,577, filed Jul. 19, 1993, abandoned.

BACKGROUND OF THE INVENTION

This invention concerns assays for measuring the ability of an oligonucleotide to hybridize to a target nucleic acid sequence, and the ability of an agent to alter a nucleic acid sequence. These assays are particularly useful for measuring the ability of an antisense oligonucleotide to hybridize to a target sequence, or a ribozyme to hybridize and cleave a target sequence, under essentially physiological conditions.

Antisense oligonucleotides and ribozymes can hybridize to a target RNA, such as mRNA, and inhibit production of protein from the mRNA. A ribozyme can hybridize to its target site and inhibit production of protein from mRNA by cleaving mRNA.

Numerous mechanisms have been proposed to explain the effects of antisense oligonucleotides. For example, see Helene and Toulme, *Biochimica et Biophysica Acta* 1049:99 (1990), and Uhlmann and Peyman, *Chemical Reviews* 90:543 (1990). These mechanisms include forming a DNA:RNA substrate for cellular RNAse H which degrades the RNA strand involved in the duplex; hybridization of antisense oligonucleotides to nascent mRNAs leading to premature transcription termination; and interfering with mRNA processing by hybridizing to a pre-mRNA intron/exon junction. These mechanisms are based upon the ability of an antisense oligonucleotide to hybridize to its target nucleic acid sequence.

Hybridization of an oligonucleotide to a target nucleic acid sequence is thought to occur by hydrogen bonding between complementary nucleotides present on the oligonucleotide and the target nucleic acid sequence. If the individual nucleotides on the target nucleic acid sequence are not accessible to the oligonucleotide hybridization will be prevented. Inaccessibility of a target nucleic acid sequence can be due to various factors, including the secondary structure of the target nucleic acid sequence or the oligonucleotide, and proteins associated with those nucleic acids.

Factors other than inaccessibility can affect hybridization of an oligonucleotide to a target nucleic acid sequence. Additional factors include the degree of complementarity between the oligonucleotide and the target nucleic acid sequence, and the hybridization conditions.

Various procedures are available for determining the ability of an oligonucleotide to hybridize to a target sequence. Some of these procedures involve hybridizing a labeled oligonucleotide to a target site and then physically separating the formed duplex from non-hybridized labeled oligonucleotide. Hybridization can be detected using a variety of techniques, such as gel electrophoresis (Southern, *J. Mol. Biol.* 98:503 (1975)); use of biotinylated DNA probes and enzyme labeled antibodies (Yehle, et al., *Molecular and Cellular Probes* 1:177 (1987)); and use of fluorescent, chemiluminescent, and enzyme labeled synthetic nucleic acid probes (Urdea, et al., *Nucleic Acids Research* 16:4937 (1988)).

Lingelbach et al., *Nucleic Acid Res.* 16:3405 (1988), mentions the use of complementary oligonucleotides to mRNA sequences in wheat germ lysate to check for accessibility of mRNA sequences. The wheat germ lysate contains endogenous RNAse H. Accessibility of mRNA was measured using polyacrylamide gel electrophoresis by determining the stability of mRNA in the presence and absence of complementary oligonucleotides.

McSwiggen et al., Abstract, 1991, describe a method for assay for ribozyme accessibility to an RNA target site. The method involves use of RNAse H to detect hybridization of RNA target with a DNA fragment.

SUMMARY OF THE INVENTION

The present invention features homogeneous assays to measure the ability of an oligonucleotide to hybridize to a target nucleic acid sequence. These assays employ a labeled nucleic acid-based probe to detect the alteration of a target nucleic acid sequence. Alteration of a target nucleic acid sequence is brought about by the formation of an oligonucleotide:target duplex, and either the addition of a duplex-altering agent or by the inherent duplex-altering ability of the oligonucleotide (e.g., one having endonuclease activity, such as a ribozyme). The labeled probe hybridizes to non-altered nucleic acid in a manner which protects probe label from subsequent chemical degradation. Alteration can then be determined by the absence of a probe label signal. Also described is a procedure for assaying the ability of an agent to alter nucleic acid.

The ability of a probe to hybridize in a manner that protects the probe label from chemical inactivation is illustrated in FIG. 1. FIG. 1 shows protected, less protected and unprotected probe label. The illustrated probe label is a covalently attached acridinium ester (AE). When the probe is hybridized with a target nucleic acid to form a duplex, the AE is protected from alkaline hydrolysis. The further the AE is located from the ends of the hybridized probe (i.e., the more centrally located), the more protected the AE. When the AE is located at the end of a duplex region (FIG. 1B), the AE is less protected. When the AE is present on single-stranded probe the AE is unprotected.

The featured assay can be used to measure the ability of an oligonucleotide to hybridize to a particular nucleic acid sequence. One use of oligonucleotides, such as antisense oligonucleotides and ribozymes, is to hybridize to a target nucleic acid sequence and prevent the target nucleic acid from being used to synthesize protein. Oligonucleotides can be targeted to nucleic acids, such as those present in bacteria, plants, humans, and viruses.

Hybridization of an oligonucleotide to a target nucleic acid sequence is affected by numerous factors including the accessibility of the target nucleic acid sequence, the structure of the oligonucleotide and the hybridization conditions. The assays described herein use one or more probes to detect the ability of a non-labeled oligonucleotide to hybridize to a target sequence under a variety of hybridization conditions, without the need to physically separate oligonucleotide fragments. Hybridization conditions such as temperature, hybridization buffer, time of hybridization and the ratio of the concentration of the oligonucleotide to the target can be set to approximate intracellular or physiological conditions, or varied independently as needed for other applications. Thus, the assay may be used to screen oligonucleotides for the ability to hybridize to target nucleic acid sequences under conditions in which the oligonucleotides would be expected to exert their effect.

Thus, in a first aspect, the invention features a homogeneous assay method which measures the ability of an oligonucleotide to form a hybrid with a target nucleic acid sequence. The assay includes the following steps: (a) contacting a test sample containing a target nucleic acid sequence with an oligonucleotide; (b) treating the test sample with a duplex-altering agent; (c) contacting the treated test sample with a labeled probe under stringent hybridization conditions in which the probe can hybridize to a non-altered single-stranded target nucleic acid sequence. The probe label is chosen such that it is protected from subsequent chemical inactivation only when the labeled oligonucleotide is hybridized to non-altered target nucleic acid. The probe cannot hybridize to an altered target nucleic acid sequence in a manner which protects the probe label from subsequent chemical inactivation. The method further includes a step (d) of measuring any hybridization of the probe to non-altered target nucleic acid sequence by measuring the amount of protected label surviving chemical treatment of the sample. Chemical treatment is carried out with a chemical able to inactivate the unprotected label. One example of such a label is an AE, much as described by Nelson et al., infra.

The test sample includes nucleic acid containing the target nucleic acid sequence. The environment of the test sample can be varied to examine hybridization under different conditions. Preferably, the environment of the test sample approximates physiological conditions where the target nucleic acid is naturally found. "Essentially physiological" refers to conditions designed to mimic a physiological or cellular environment. At a minimum, essentially physiological conditions include a solution buffered to physiological pH, and having a physiological temperature. Preferably, physiological conditions approximate physiological protein concentration and composition, nucleic acid concentration, and salt concentration and composition.

The oligonucleotide to be used in the described assay is typically designed to be complementary to the target nucleic acid sequence. The degree of complementarity and the size of the oligonucleotide are variable. One use of the assay is to determine the ability of an oligonucleotide to hybridize to a target nucleic acid sequence.

A feature of the described assays is the ability of a labeled probe to hybridize to non-altered target sequence in a manner protecting the probe label from subsequent chemical inactivation. Alteration of the target sequence can be carried out using duplex-altering reagents able to cut, degrade, or chemically alter nucleic acids. Examples of duplex-altering reagents include DNAses, RNAses, restriction enzymes, chemical reagents, and triple-strands equipped with chemical reagents able to cleave nucleic acid.

The preferred duplex-altering reagent is a substance which selectively degrades the target sequence of an oligonucleotide:target duplex or breaks a covalent bond in the target strand of the duplex, and will not degrade or alter single-stranded target sequence. If single-stranded target sequence is no longer present due to the action of the duplex altering agent, the probe cannot hybridize at all and as a result, the probe label will not be protected from chemical inactivation. In this instance, the assay would not be able to measure the formation of an oligonucleotide:target duplex based on detection of altered targeted nucleic acid because the removal of target sequence would indicate alteration of the target sequence whether or not an oligonucleotide:target duplex formed. Preferably, the target nucleic acid is RNA, the oligonucleotide is DNA wherein the nucleotides are joined by phosphodiester or phosphorothioate groups, and the duplex-altering agent is RNAse H.

The labeled probe is used to detect the presence of non-altered target sequence. Probes are labeled oligonucleotides having sufficient contiguous bases complementary to the target nucleic acid sequence to hybridize to the unaltered target nucleic acid sequence under stringent hybridization conditions. Suitable labels do not prevent hybridization under appropriate stringent hybridization conditions, but exhibit different characteristics in a bound (probe:target) versus unbound state, and can be readily detected. An example of a useful characteristic for a label is increased resistance to alkaline hydrolysis in a bound state, but not when in an unbound state. Probes are preferably, 8 to 100 nucleotides in length, more preferably 14 to 50 nucleotides in length.

Acridinium ester is the preferred label. Chemiluminescence from AE can be measured as described by Arnold et al., entitled "Homogeneous Protection Assay," EPO application number 88308767.8, publication number 309230, hereby incorporated by reference herein and Nelson et al., in *Nonisotopic DNA Probe Techniques,* p. 275 Academic Press, San Diego (Kricka, ed., 1992) hereby incorporated by reference herein (including all chemical formulae for AE). Arnold et al., supra, provides numerous examples of acridinium esters which can be used in a homogeneous protection assay. These acridinium esters can also be used as a probe label for the methods described herein. FIG. 2 illustrates differential hydrolysis of protected and not protected AE-label, and chemiluminescence from protected AE-label. Chemiluminescence can be brought about for an AE group by the addition of $H_2O_2$ and alkaline solution.

The AE group in an AE labeled probe is preferably positioned 3 or more nucleotides from the end of the AE-probe. More preferably, the AE group is positioned 7 nucleotides from the end of the AE-probe. Most preferably, the AE group is positioned at least 10 nucleotides from the ends of the AE-probe. As noted above, as the AE group is closer to the end of the AE-probe it is less protected from chemical inactivation.

FIG. 3 illustrates the preferred assay. A phosphorothioate oligodeoxynucleotide is contacted with an RNA target sequence at 37° C. RNAse H is then added to form a test sample (designated "+"). The control sample lacks RNAse H (designated "−"). An AE-labeled probe is then used under stringent hybridization conditions to detect the presence of any remaining target sequence. If the antisense oligodeoxynucleotide hybridized to the target in the test sample, the target nucleic acid will be degraded by RNAse H, and the sample no longer has a target sequence for subsequent hybridization with the probe. Thus, in the test sample, the AE label is present predominately, or only, as single-stranded nucleic acid. A chemical inactivating agent is then added to hydrolyze any unprotected label ester groups. As a result of the chemical inactivation, a loss of AE signal occurs. This signal is compared to the control, which is not treated with RNAse H. The control sample has non-altered target sequences that can form a duplex with the probe, thereby protecting the probe AE label.

The assay can also be carried out if only part of the target nucleic acid sequence is degraded or altered. The partial alteration of target nucleic acid sequence is detected using a labeled probe, wherein the probe label is positioned so it will not be protected from subsequent chemical inactivation if the probe hybridizes to only one part of the cut target site. The probe label is located on the probe at a position complementary to the cut target site (see FIG. 1), or on a short probe region which will not hybridize well under stringent hybridization conditions to a cut target site.

An example of the use of an AE-labeled probe to detect a cut target site is shown in FIG. 4. The probe shown in FIG.

4 is labeled on a short region which is not involved in hybridization to a cleaved target site. The short probe region does not have a sufficient number of complementary nucleic acid sequences to enable it to hybridize to the cut target site under appropriate stringent hybridization conditions.

Preferably, the short probe region has 3 to 10 nucleotides complementary to one part of the cut target site, and the remaining nucleotides are complementary to the other part of the cut target site. The probe label is preferably positioned 3 to 7 nucleotides from the end of the short probe region. More preferably, the label is positioned 7 nucleotides from the end of the probe.

In a related aspect, the assay is carried out using a treated test sample and a control sample. The treated test sample is treated with a duplex-altering agent, while the control sample is not treated with a duplex-altering agent. Both samples are then probed for the presence of non-altered target nucleic acid sequence. The use of a control sample is preferred as a means of measuring hybridization to a target nucleic acid sequence and confirming that the absence of detectable probe hybridization is not due to an experimental flaw. Other proper controls include use of duplex-altering agent in the absence of complementary oligonucleotide.

In another related aspect, a method is described for assaying the ability of a ribozyme to cleave a target nucleic acid sequence. The ribozyme is introduced into a sample containing the target nucleic acid sequence. A probe is then used to measure the presence of cleaved RNA. The amount of chemiluminescence in the presence of a ribozyme can be compared to a control where no ribozyme is added to the test sample.

The ribozyme cleavage assay is carried out essentially as shown in FIG. 5. The probe used to determine ribozyme cleavage of a target site is designed as described above for determining partial alteration of a cut target site (i.e., placing the label opposite the cut target site or on the short probe region).

In another aspect, an assay is described for measuring the ability of an agent to alter a nucleic acid sequence. The assay is carried out by contacting a target nucleic acid with the agent and then using a labeled probe to measure the degree of alteration. The labeled probe is used to detect the presence of non-altered nucleic acid, as described above, by predominately hybridizing to non-altered nucleic acid in a manner which protects the probe label from subsequent chemical inactivation.

This assay can measure different types of alterations such as nuclease degradation, restriction enzyme cutting, and chemical alteration of the purine or pyrimidine rings to a form which can no longer hydrogen bond. Proper probe design for this assay depends upon the type of agent being assayed. If the agent cuts or chemically alters only at a few sites, the probe label is preferably placed on the probe across from the cut or altered site, as described above (see FIG. 1). Alternatively, a cut site can be assayed using a probe having a short labeled region that does not hybridize to the cleaved nucleic acid target as described above (see FIG. 4).

This assay can measure the ability of an agent to alter a nucleic acid sequence in a homogenous assay using a labeled probe without the need to physically separate altered from non-altered nucleic acid. Thus, the ability of various agents, such as nucleases, restriction enzymes, and chemicals, to alter nucleic acid can be readily determined.

In another aspect, kits for carrying out the methods described herein are described. The kits are made of a probe label and a duplex altering agent in separate containers. Preferably, the probe label contained in the kit can be protected from chemical inactivation when in a bound state. More preferably, the probe label is an acridinium ester and the duplex altering agent is RNAse H.

Other features and advantages of the invention will be apparent from the following description of the preferred embodiments thereof, and from the claims.

BRIEF DESCRIPTION OF THE DRAWINGS

FIG. 1 illustrates protected and unprotected acridinium ester. The "p" refers to a phosphodiester group.

DESCRIPTION OF THE PREFERRED EMBODIMENTS

Figure 2:
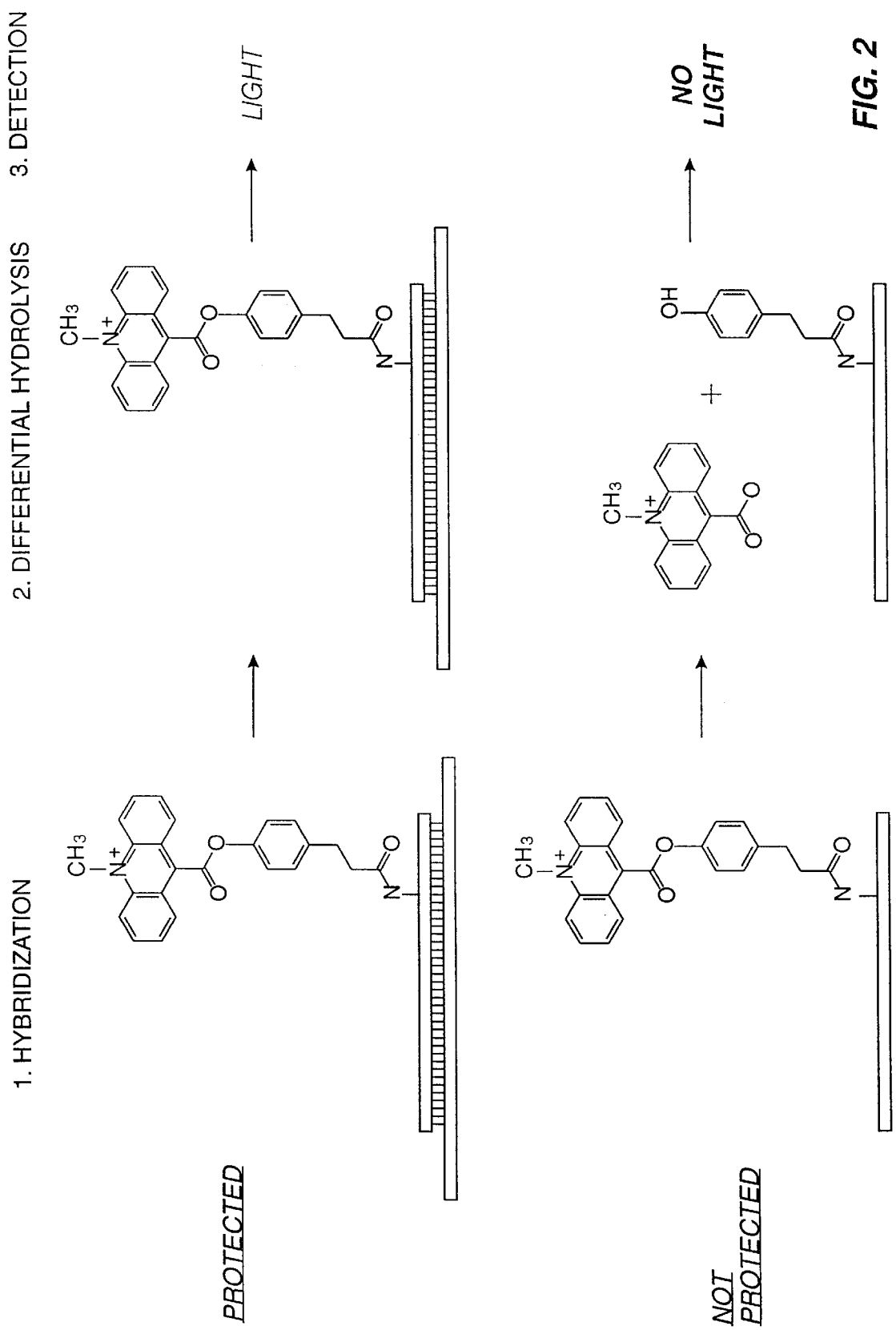
FIG. 2 illustrates the detection of an acridinium ester. Differential hydrolysis results in cleavage of unprotected acridinium ester present in unhybridized probe. Chemiluminescence from protected acridinium ester is then measured (light).
Figure 3:
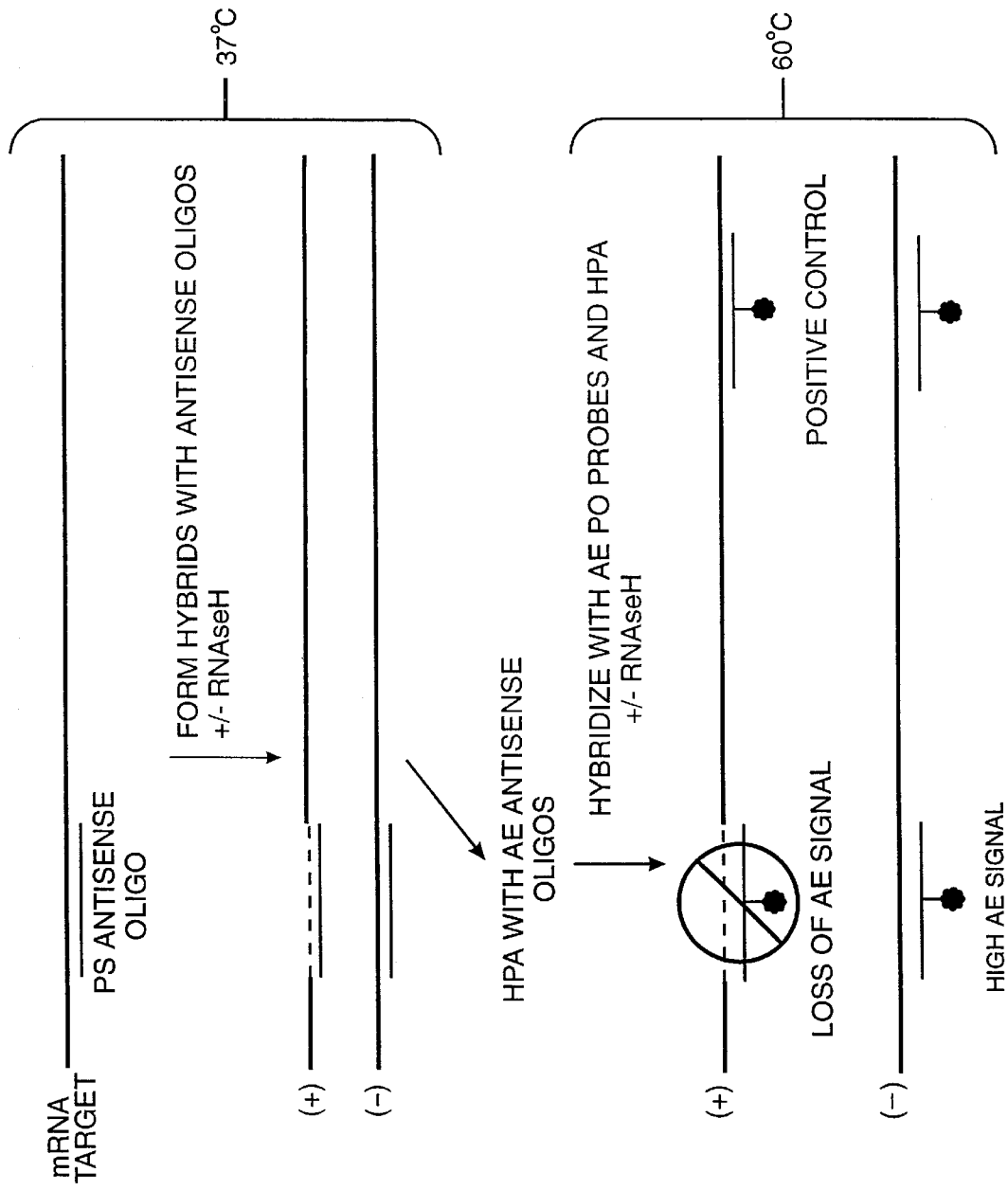
FIG. 3 illustrates the preferred method of assaying for hybridization of an oligonucleotide to a target sequence using acridinium ester labeled probe. "+" refers to the presence of RNAse H. "−" refers to the absence of RNAse H.
Figure 4:
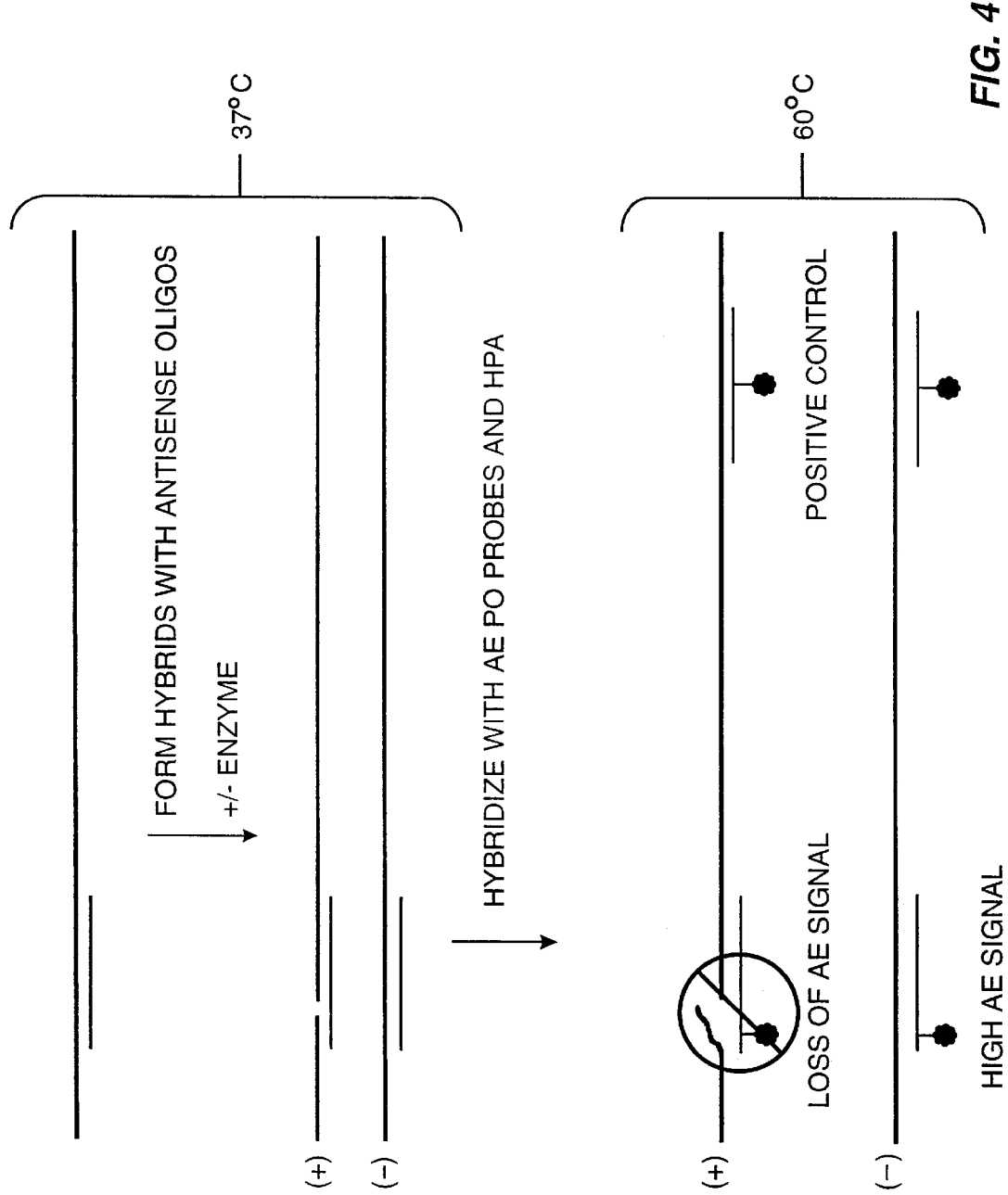
FIG. 4 illustrates an assay which measures cleaved nucleic acid using a probe having a short labeled probe region that does not hybridize to the cleaved nucleic acid target.
Figure 5:
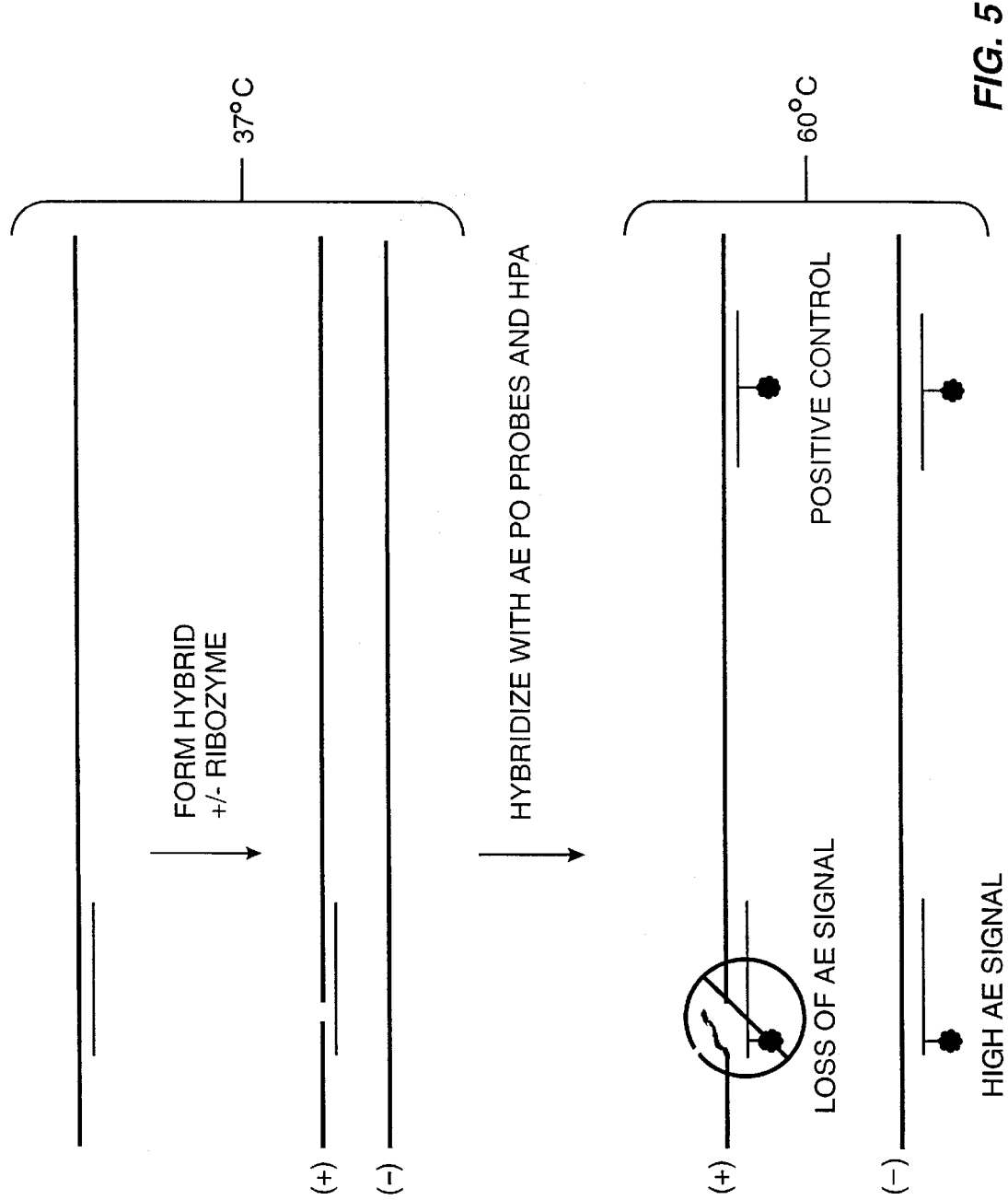
FIG. 5 illustrates an assay to measure target site cleavage by a ribozyme. Altered nucleic acid is detected using a probe having a short probe region.

The featured methods can be used to assay the hybridization of an oligonucleotide to a particular nucleic acid sequence. These methods are particularly useful for assaying hybridization of antisense oligonucleotides to their target RNA nucleic acid sequences under essentially intracellular or physiological conditions. The described assay can be used to rapidly and quantitatively screen and rank antisense oligonucleotides for a given target and is generally applicable to any oligonucleotide:target system. Also described are methods for assaying the ability of ribozymes to hybridize and cleave a target nucleic acid sequence, and assaying the ability of an agent to alter nucleic acid.

Oligonucleotides, such as antisense oligonucleotides and ribozymes, can be used to alter gene expression in vivo. Such alteration can be carried out in different organisms to achieve different objectives. For example, oligonucleotides can be used to obtain desirable plant traits, or used in humans as therapeutic agents.

For an oligonucleotide to be used successfully in an organism it must be able to hybridize to its target nucleic acid sequence under physiological conditions. Numerous factors can affect the ability of an oligonucleotide to hybridize to a target nucleic sequence. These factors, include the accessibility of the target nucleic acid, the structure of the oligonucleotide and the conditions under which hybridization occurs.

A target region can be inaccessible due to various factors such as secondary structure and proteins associated with the target nucleic acid. These factors may prevent an oligonucleotide from hydrogen bonding, and hybridizing, to a target sequence.

The structure of the oligonucleotide includes the type of linkages joining the nucleotide groups, the presence or absence of a label, the degree of complementarity between the oligonucleotide and the target nucleic sequence, modifications of the sugar and purine or pyrimidine base and the secondary structure of the oligonucleotide. The degree of complementarity includes the number of mismatches between the oligonucleotide and target sequence, and the total number of complementary nucleotides. The smaller the number of contiguous complementary nucleotides, and the greater the number of mismatches, the less likely hybridization would be expected to occur.

The hybridization conditions includes the hybridization buffer (e.g., pH, salt concentrations, and protein concentration) and the temperature. If the oligonucleotide is to be used as a therapeutic, the hybridization conditions should be designed to approximate the conditions under which the oligonucleotide will be used.

The factors listed above affecting hybridization are interrelated. For example, as the hybridization temperature increases the degree of complementarity between an oligonucleotide and a target nucleic acid sequence may need to be increased for hybridization to occur. Hybridization will be inhibited if there is not sufficient complementarity to yield a duplex with a higher melting temperature than the hybridization temperature.

The described assay can be used to determine whether a sufficient degree of complementarity exists under a given set of conditions to form a duplex, and whether other factors such as accessibility of the target region will prevent hybridization. Hybridization of an oligonucleotide to its target sequence is preferably carried out by first contacting a test sample containing a target nucleic acid sequence with the oligonucleotide. Preferably, the oligonucleotide is made up of nucleotide containing deoxyribose moieties, and is connected by one or more phosphorothioate or phosphodiester linkages, the target nucleic acid sequence is RNA or mRNA, and an enzyme that degrades the RNA strand of a RNA:DNA hybrid is used. After the oligonucleotide is contacted with the test sample the reactions are preferably divided and incubated further in the presence and absence of a RNAse H such as the E. coli RNAse H, or calf thymus RNAse H. These reactions are then diluted, and the relative amount of non-altered target RNA is measured by the Homogeneous Protection Assay (HPA) using AE-labeled probe, as described by Nelson et al., supra. With different experimental designs, the present invention can be expanded to determine the extent of hybridization and the hybridization kinetics.

There is no intention to limit the present invention to the preferred assay or to the specific examples provided herein. Variations of the preferred assay are disclosed in the present application. Additional variations can be carried out based on the present disclosure by one skilled in the art. Various components of the described assay and specific examples are detailed below.

Targeted Oligonucleotide

"Targeted oligonucleotide" refers to an oligonucleotide designed to hybridize to a particular nucleic acid sequence. The length and degree of complementarity of a targeted oligonucleotide to its target sequence is variable. One of the uses of the disclosed assay is to determine whether a targeted oligonucleotide can hybridize to a particular target sequence.

The sugar groups of a targeted oligonucleotide may be ribose, deoxyribose, or have a modified sugar group. In addition, the heterocyclic base (e.g., adenine, cytosine, guanine, uracil or thymine) may be modified. The nucleotides can be joined by phosphodiester linkages or modified linkages such as phosphorothioate and methylphosphonate. Oligonucleotides containing modified nucleotides should be able to hybridize with their target sequences and should not prevent alteration of the target sequence with a duplex-altering agent.

The preferred duplex-altering agent is RNAse H. Thus, the preferred targeted oligonucleotide should be chosen so it will allow cleavage of the target RNA nucleic acid. An RNA target strand can be cleaved with RNAse H when the hybridized oligonucleotide is DNA containing one or more phosphorothioate or phosphodiester linkage. The RNA strand will not be cleaved with RNAse H when the hybridized oligonucleotide has only linkages such as methylphosphonate and phosphoramidate.

Alteration of Duplex

Hybridization of an oligonucleotide to a target sequence is measured by adding an agent which alters oligonucleotide:target duplexes which may have formed under the tested hybridization conditions, and then using a probe to assay the amount of remaining non-altered duplex. A suitable duplex-altering agent degrades or cleaves the target nucleic acid sequence of an oligonucleotide:target duplex. Examples of suitable altering agents include DNAses which degrade double stranded DNA, RNAses such as RNAse III which degrade double-stranded RNA, RNAses such as RNAse H which degrade the RNA strand of RNA:DNA duplex, and restriction enzymes. Altering agents which act on specific nucleic acid sequences should be used only on target nucleic acid having the specific sequence. For example, restriction enzymes act on specific nucleic acid sequences and RNAse III has considerable sequence specificity. Useful duplex-altering agents are those active only on duplex nucleic acid, and not on single-stranded nucleic acid. Preferably, such agents act only on duplex created in the presence of the target and oligonucleotide probe, e.g., an RNA:DNA hybrid. Such agents are well known in the art and their ability readily assessed using standard methodology.

The choice of a suitable duplex-altering agent will partly depend upon the sugar groups of the oligonucleotide and target nucleic acid sequences. Preferably, RNAse H is used to alter the oligonucleotide:target duplex, the oligonucleotide contains deoxyribose sugar groups, and the target nucleic acid sequence contains ribose moieties.

Ribozymes act on single-stranded RNA (and sometimes DNA) and can cleave RNA at specified target sequences. The term "ribozyme" refers to nucleic acid molecules having an intermolecular nucleic acid cleaving activity, e.g., the ribozyme is able to cleave a covalent bond in an RNA or single-stranded DNA molecule. Thus, a separate duplex-altering step is not needed if the assay is used to measure the ability of a ribozyme to cleave its target sequence. Indeed, the duplex formed by a ribozyme and its target nucleic acid is altered by the ribozyme itself cleaving the target nucleic acid.

Detection Of Non-Altered Target Sequence

Non-altered target nucleic acid sequences can be detected using probes and measuring the formation of probe:target, which protects the probe label. A probe is a labeled oligonucleotide having sufficient contiguous nucleotides complementary to its target nucleic acid sequence to form a probe:target duplex under stringent hybridization conditions. Probes are preferably, 8 to 100 nucleotides in length, more preferably 14 to 50 nucleotides in length.

The sugar groups of a probe may be ribose, deoxyribose, or have a modified sugar group. In addition, the heterocyclic base (e.g., adenine, cytosine, guanine, uracil, or thymine) may be modified. The nucleotides can be joined by phosphodiester linkages or modified linkages such as phosphorothioate and methylphosphonate. Oligonucleotides containing modified nucleotides should be able to hybridize with their target sequences.

Suitable labels are those which do not prevent hybridization under appropriate stringent hybridization conditions, exhibit different characteristics in a bound (probe:target) versus unbound state, and may be readily detected. Different characteristics may include increased resistance to alkaline hydrolysis in a bound state. The use of labeled probes to determine duplex formation is described by Arnold et al., supra, entitled "Homogeneous Protection Assay," and Nelson et al., supra. These references illustrate the use of AE-labeled probes to detect target nucleic acid sequences in a homogeneous protection assay. Arnold et al., supra, also provides examples of acridinium esters which can be used as a probe label.

The essential steps of HPA are (1) hybridization, (2) differential hydrolysis (inactivation), and (3) detection. In addition to these steps, nucleic acid may be denatured prior to using the probe to render target nucleic acid more accessible to the probe. Target nucleic acid may be inaccessible to the probe for the same reasons it may be inaccessible to a targeted oligonucleotide. Denaturation of target nucleic acids may be carried out in the same manner as denaturation of double stranded nucleic acid as described by Nelson et al., supra. The use of helper probes as described by Hogan et al., U.S. Pat. No. 5,030,557, hereby incorporated by reference herein, is another way to open up an inaccessible region.

A separate denaturation step and/or the use of helper probes are not required if the probe can hybridize to its target sequence under stringent hybridization conditions. Stringent hybridization conditions may render the target sequence accessible.

The probe detects hybridization of an oligonucleotide by hybridizing to non-altered target nucleic acid sequence in a manner protecting the probe-label from subsequent chemical inactivation. Subsequent chemical inactivation refers to the use of an agent to selectively inactivate unprotected label so it is no longer detectable. AE-labeled probes may be chemically inactivated as described by Nelson et al., supra, and Arnold et al., supra.

The probe label should be placed on the probe to achieve maximal protection when in a bound state. Maximal protection is achieved by placing the probe label away from the ends of the probe. Probe label located within three nucleotides from the end of a probe may not be well protected from subsequent chemical inactivation, even if in a bound state. Preferably, the label is placed 3 or more nucleotides from the end of the probe. More preferably, the label is placed 7 or more nucleotides from the end of the probe. Most preferably, the label is placed 10 or more nucleotides from the end of the probe. The degree to which a bound probe-label is protected can be determined using HPA.

Hybridization of probe to target is preferably carried out under stringent hybridization conditions. Stringent conditions are those in which the probe can hybridize to its target nucleic sequence and not to other nucleic acid sequences present in the test sample. Suitable stringent hybridization conditions may be determined by techniques known in the art. For example, Nelson et al., mention stringent hybridization conditions for use with AE-labeled phosphodiester probes comprising: 0.1M lithium succinate buffer, pH 5.0, 2 mM EDTA, 2 mM EGTA, 10% (w/v) lithium lauryl sulfate, and incubation at 60° C. for 5 to 60 minutes.

Hybridization of the probe should be carried out under conditions favoring hybridization of probe to target versus hybridization of the targeted oligonucleotide to target. Hybridization of the probe can be favored by designing the probe such that the probe:target has a higher melting temperature (Tm) than oligonucleotide:target. The label inactivation step of the assay could then be run at a temperature between the Tm of the probe and the oligonucleotide. For example, if the Tm of the targeted oligonucleotide was 50° C. and that of the probe was 60° C., the inactivation step could be run at 55° C. or even 58° C. (58° C. would give better discrimination but lower signal from the probe).

Probes having a higher Tm can be designed based upon techniques known in the art, such as by increasing the number of contiguous complementary nucleotides of the probe to target relative to that of the targeted oligonucleotide to target or using phosphorothioate oligonucleotides and phosphodiester probes. The Tm difference between probe and oligonucleotide is preferably 3° C., more preferably 7° C., and most preferably 10° C. or more.

Increasing the ratio of probe to targeted oligonucleotide will also favor probe:target hybridization. A 2-fold excess would be adequate to see some difference in hybridization especially if the label used was very sensitive (such as with the AE). A 10-fold difference would give a very distinct and clearly discernible difference in hybridization, and with a 100-fold difference the amount of oligonucleotide:target should be negligible.

Another way of favoring probe target hybridization is though the use of a DNAse to remove the targeted oligonucleotide. This procedure may be used when the targeted oligonucleotide is DNA and the target nucleic acid is RNA. Suitable DNAses for this procedure can degrade single stranded DNA but not RNA. It is important that the chosen DNAse be free of contaminating RNAse activity which may degrade the target nucleic acid sequence. Preferably, a DNAse step is used to remove targeted oligonucleotide when both the targeted oligonucleotide and the target nucleic acid are joined by phosphodiester linkages.

Differential hydrolysis is carried out to preferentially hydrolyze unbound label. Nelson et al. supra, describe determining differential hydrolysis conditions for use with AE-labeled probes. These conditions involve alkaline hydrolysis of unprotected AE. Intact AE can be made chemiluminescent using techniques known in the art such as hydrogen peroxide under alkaline conditions. Chemiluminescence can be measured in a luminometer (e.g., LEADER I®, LEADER 50®, LEADER 250® and LEADER 450®, available from Gen-Probe Incorporated).

Assaying The Ability Of An Agent To Alter Nucleic Acid

The ability of an agent to alter nucleic acid can be assayed by contacting a target nucleic acid with the agent and then measuring the extent of alteration using a labeled probe. These procedures are carried out essentially as described above for assaying the ability of a ribozyme to hybridize and cleave a target site, with the ribozyme being replaced with one or more nucleic acid altering agents.

Proper design of probes which detect alteration of nucleic acid should take into account the type of agent being tested. If the agent degrades nucleic acid, such as a nuclease, the probe label should placed away from the ends of the probe to obtain maximum protection upon hybridization. If the agent cuts the nucleic acid, such as a restriction enzyme, the probe label should be placed across from the cut target site, or on a short probe region. Alternatively, if the agent alters nucleic acid by disrupting hydrogen bond formation, such as by altering the heterocyclic purine or pyrimidine ring, the probe label should be positioned across from the altered nucleotide.

Oligonucleotide Synthesis

Oligonucleotides containing phosphodiester or modified linkages can be synthesized by standard techniques. These techniques include the synthesis of oligonucleotides containing phosphodiester linkages (Caruthers, et al., in *Methods In Enzymology* 154:287 (1987)), phosphorothioate linkages (Bhatt, U.S. Ser. No. 07/319,570 entitled "Method and reagent for sulfurization of organophosphorous compounds" filed Mar. 6, 1989, assigned to Gen-Probe Incorporated, the assignee of the present invention, and hereby incorporated by reference herein), and methylphosphonate linkages (Klem et al ., entitled "Improved process for the synthesis of oligomers" PCT WO92/07864).

Probe labelling with AE is preferably carried out as described by Nelson et al., supra, or Arnold, et al., (PCT/US88/03361), entitled "Acridinium Ester Labelling and Purification of Nucleotide Probes," hereby incorporated by reference herein.

Examples are provided below to illustrate different aspects and embodiments of the present invention. These examples are not intended in any way to limit the disclosed invention.

EXAMPLE 1

The use of the present invention to measure hybridization of an oligonucleotide to a target sequence present in rabbit globin mRNA is described below. The targeted oligonucleotide used in this example, BglR38-PS, contains phosphorothioate linkages and has the following nucleotide sequence, written 5' to 3' SEQ ID NO. 1.

The nucleic acid sequence of the probe used in this example, AE-BglR38-PO (SEQ ID NO. 5), has the same nucleic acid sequence as BglR38-PS (SEQ ID NO. 5) but the nucleotides of the probe contain phosphodiester linkages, and an AE is attached between nucleotides 11 and 12. oligonucleotides containing phosphodiester linkages were synthesized using standard phosphoramidite solid-phase chemistry (Caruthers, et al., supra). Oligonucleotides containing phosphorothioate linkages were synthesized by joining nucleotides using standard phosphoramidite solid-phase chemistry and carrying out sulfurization at each step of the growing chain according to the method of Bhatt, supra. BglR38-PO (SEQ ID NO. 5) was labeled with acridinium ester and purified as described by Nelson, et al., supra.

The ability of AE-BglR38-PO (SEQ ID NO. 5) to detect a target sequence was characterized prior to determining the ability of BglR38-PS to hybridize to its target sequence. The general HPA protocol described by Nelson et al. was used for this purpose. Hybridization of AE-BglR38-PO (SEQ ID NO. 5) to rabbit globin mRNA was carried out using 0.9 pmoles of rabbit globin mRNA, 0.1 pmol AE-BglR38-PO (SEQ ID NO. 5), in 100 μL of hybridization buffer (0.1M lithium succinate buffer, pH 5.0, 2 mM EDTA, 2 mM EGTA, 10% (w/v) lithium lauryl sulfate).

The half-life of non-hybridized and hybridized probe was determined as described by Nelson et al., supra, by measuring the loss of chemiluminescence versus time. The log of the percentage of chemiluminescence remaining after a given time was plotted against the given time. The half-life was then determined by linear regression analysis. The percentage of hybridization was determined from the y-intercept of the linear portion of the hydrolysis curve.

Tm was determined by mixing excess target with probe to form a probe:target hybrid in a lithium succinate buffered solution (0.1M lithium succinate buffer, pH 5.0, 2 mM EDTA, 2 mM EGTA, 10% (w/v) lithium lauryl sulfate). Aliquots of the hybrid were diluted in the hybridization buffer and incubated for five minutes at various temperatures starting below that of the anticipated Tm (55° C.) and increasing in 2–5 degree increments. This solution was then diluted with a mild alkaline borate buffer (0.15M sodium tetraborate, pH 7.6, 5% (v/v) Triton X-100) and incubated at a lower temperature (50° C.) for ten minutes. Under these conditions the AE attached to a single-stranded probe is hydrolyzed while the AE attached to hybridized probe is relatively protected from hydrolysis. The amount of AE remaining is proportional to the amount of hybrid and can be measured by the chemiluminescence produced from the AE upon the addition of hydrogen peroxide and alkaline solution. The resulting data was plotted as percent of maximum signal (usually from the lowest temperature) versus temperature. The Tm is defined as the temperature at which 50% of the maximum signal remains.

TABLE 1

| Oligomer | Hyb Temp (°C.) | % Hyb | Tm (°C.) | (Half life (min)) Non-hybridized | Hybridized |
|---|---|---|---|---|---|
| Probe | 60 | 98.8 | 67 | 0.35 | 13.1 |

As shown by the increased half-life of hybridized probe, AE-BglR38-PO hybridizes to target sequence in a manner which protects the AE label from alkaline hydrolysis. The results indicate that AE-BglR38-PO can be used to detect its target sequence under the conditions employed.

The suitability of other probes and the desired conditions for hybridization of probe to target sequence can be determined using techniques described herein and as described in the art, as in for example, McDonough et al., entitled "Detection Of Human Immunodeficiency Virus Type 1" U.S. Ser. No. 8/040,745 filed Mar. 26 1993, abandoned, assigned to Gen-Probe Incorporated, the assignee of the present invention, and hereby incorporated by reference herein.

The ability of the targeted oligonucleotide to hybridize to its target nucleic acid was determined by mixing targeted oligonucleotide for 2 hours at 37° C. with rabbit globin mRNA at a molar ratio of either 1:1 or 1:3 (mRNA:oligonucleotide). A control with no targeted oligonucleotide was also included. Hybridization was performed in 2×*E. coli* RNAse H buffer (40 mM Tris-HCl (pH 7.5), 20 mM MgCl$_2$, 200 mM KCl, 0.2 mM DTT and 10% (w/v) sucrose).

The reactions were then divided and an equal volume of water added to make duplicates at 1× final buffer concentration for optimal RNAse H enzyme activity. *E. coli* RNAse H (BRL, 0.4 U/reaction) was added to one of the two duplicate reactions (test sample). The other duplicate reaction lacking RNAse H served as the (−) RNAse H control. These reactions were incubated at 37° C. for 1 hour, stopped by denaturing at 95° C. for 5 minutes, and placed directly on ice.

Aliquots of the reactions were then assayed with AE-BglR38-PO (SEQ ID NO. 5) according to the general protocol described by Nelson, et al. supra. The results are shown in Table 2 (the data represent averages of duplicate analyses).

TABLE 2

| | RLU mRNA: Oligonucleotide | | |
|---|---|---|---|
| | 1:0 | 1:1 | 1:3 |
| − RNAse H | 277818 | 298980 | 333312 |
| + RNAse H | 213628 | 8666 | 5529 |

The data shown in Table 2 demonstrate that at both 1:1 and 1:3 ratio of mRNA to oligonucleotide, the probe hybridized to the target and RNAse H subsequently digested the mRNA strand of the oligonucleotide:mRNA hybrid. The retention of signal (within experimental error) in the absence of BglR38-PS but in the presence of mRNA and RNAse H demonstrate that the loss of signal at 1:1 and 1:3 (mRNA to oligonucleotide) is not a non-specific RNAse H effect.

These results show that the described assay is capable of rapidly determining whether an oligonucleotide in question hybridizes with a particular target nucleic acid sequence.

EXAMPLE 2

The methods and oligonucleotides described in Example 1 were used to measure hybridization of a targeted oligonucleotide to a target nucleic acid sequence in 2× RNAse H buffer (Table 3, "2×") and physiological buffer (10 mM Na$^+$, 13 mM Mg$^{++}$, 160 mM K$^+$, Tris-HCl pH 7.2, 1 mM Ca$^{++}$, 100 µg/ml BSA) (Table 3, "Phy") Hybridization in physiological buffer was directly compared with hybridization in 2× E. coli RNAse H buffer from Example 1, at 1:0 (control) and 1:3 ratio of mRNA to oligonucleotide, according to the protocol described in Example 1. The results are shown in Table 3 (the data represent averages of duplicate analyses).

TABLE 3

| | RLU mRNA: Oligonucleotide | | |
|---|---|---|---|
| | 1:0 Phy | 1:3 Phy | 1:3 2× |
| − RNAse H | 310295 | 307409 | 305336 |
| + RNAse H | 281620 | 12310 | 14409 |

These results show that the described assay is capable of rapidly determining whether an oligonucleotide in question hybridizes with a particular target nucleic acid sequence under essentially physiological conditions. For the oligonucleotides tested, hybridization in 2× RNAse H buffer was equivalent to hybridization in physiological buffer.

EXAMPLE 3

This example further details the use of the procedures described herein to measure hybridization of oligonucleotides to a target nucleic acid sequence, and further demonstrates that in the preferred assay involving RNAse H, degradation depends upon both the antisense oligonucleotide and RNAse H. Various phosphodiester and phosphorothioate oligonucleotides targeted to rabbit globin mRNA were synthesized as described in Example 1. The nucleotide sequences of the synthesized oligonucleotides, written 5' to 3', are as follows:

AglR72 (13/14) (SEQ ID NO. 2) CCGATCTTTTC-CCAGGCAGTC

AglR17 (7/8) (SEQ ID NO. 3) CCATGGTGGTTCCT-TCTCAGTCGG

AglR123 (SEQ ID NO. 4) CCCAAGAACATCCTCTC-CACG

BglR38 (10/11) (SEQ ID NO. 5) GCACCATTCTGTCT-GTTTTGGGG

BglR120 (9/10) (SEQ ID NO. 6) CAGGGCCTCACCAC-CAACTTC

BglR179 (SEQ ID NO. 7) CAGGTCCCCAAAG-GACTCGAAG

The number in parenthesis refers to the position of an AE group when present. For example, (9/10) refers to the placement of an AE group between the ninth and tenth nucleotide.

Hybridization characteristics and Tm's were determined under various conditions using an acridinium ester label attached to each oligonucleotide as described in Example 1.

Oligonucleotides were hybridized at various temperatures in the presence of excess mRNA target as described in Example 1. After hybridization, the samples were incubated at 60° C. with 0.15M sodium tetraborate, pH 7.6, 5% (v/v) Triton X-100 or at 37° C. with 0.6M boric acid pH 8.5, 1% Triton X-100, to chemically inactivate the AE label. AE hydrolysis rates, Tm's and extents of hybridization were measured as described in Example 1.

The AE hydrolysis rates, the percent hybridizations and the Tm's of various phosphodiester and phosphorothioate oligonucleotides hybridized to mRNA targets are summarized in Table 4.

TABLE 4

| | | | | Half-life (min) | |
|---|---|---|---|---|---|
| Oligomer | Hyb Temp (°C.) | % Hyb | Tm (°C.) | Non-hybridized | Hybridized |
| BglR38-PO | 60 | 98.8 | 67 | 0.35 | 13.1 |
| BglR120-PO | 60 | 77.1 | 62 | 0.36 | 8.5 |
| AglR72-PO | 60 | 45.1 | <64 | 0.35 | 7.5 |
| AglR17-PO | 60 | 83.4 | 68 | 0.30 | 9.8 |
| BglR38-PO | 37 | 97.1 | | 0.32 | 14.4 |
| BglR120-PO | 37 | 45.5 | | 0.28 | 11.4 |
| AglR72-PO | 37 | 55.9 | | 0.28 | 10.9 |
| AglR17-PO | 37 | 53.6 | | 0.25 | 13.4 |
| BglR38-PS | 37 | 85.3 | 52 | 0.48 | 20.6 |
| BglR120-PS | 37 | 17.1 | <40* | 0.42 | 10.2 |
| AglR72-PS | 37 | 13.1 | <40* | 0.53 | 9.4 |
| AglR17-PS | 37 | 20.3 | <40* | 0.36 | 17.1 |

All four phosphodiester-AE (PO-AE) probes hybridized well at 60° C. BglR38-PO and phosphorothioate oligonucleotides showed the highest extent of hybridization (97.1% and 85.3%, respectively) at 37° C. The remaining PO-AE probes showed an average of only 50% hybridization, whereas the corresponding phosphorothioate-AE (PS-AE) probes averaged 16.1% hybridization under these conditions.

The Tm's obtained for the phosphorothioate oligonucleotides were significantly lower than their phosphodiester counterparts. The Tm difference between the phosphodiester and phosphorothioate oligonucleotides was exploited in the development of the probe detection step. To reduce competition between the oligonucleotide and the probe, a phosphorothioate oligonucleotide along with its corresponding PO-AE probe were used.

Hybridizations of oligonucleotides to their target nucleic acid sequences were carried out as described in Example 1 using either 2× E. coli RNAse H buffer or physiological buffer. Various concentrations of phosphorothioate and phosphodiester oligonucleotides were hybridized with mRNA at 37° C. for 2 hours. The reactions were then divided to make duplicates at 1× final buffer concentration for optimal RNAse H enzyme activity. E. coli RNAse H (BRL, 0.4 U/reaction) was added to one of the two duplicate reactions; the other duplicate reaction lacking RNAse H served as the (−) RNAse H control. The reactions were incubated at 37° C. for 1 hour, stopped by denaturing at 95° C. for 5 minutes, and placed directly on ice.

Aliquots of the reactions were then hybridized with the appropriate phosphodiester AE-probe. The AE-probe was hybridized at 60° C. for 1 hour as described in Example 1. Control hybridizations were performed using AE-probes expected to hybridize to a region other than the target nucleic acid sequence. These control hybridizations measure non-specific RNAse H degradation of mRNA target by determining whether sequences not targeted by the oligonucleotide are degraded by RNAse H. Aliquots were then diluted in hybridization buffer and 50 μL replicates were hydrolyzed in 12×75 mm luminometer tubes with 300 μL of 0.15M sodium tetraborate, pH 7.6, 5% (v/v) Triton X-100 at 60° C. until non-hybridized PO-AE control was fully hydrolyzed (usually 6–8 minutes). Chemiluminescence was brought about using a single injection of 1.5N NaOH, 0.1% $H_2O_2$ and measured in a luminometer.

Differences in hybridization properties and RNAse H susceptibilities among the different phosphorothioate antisense oligonucleotides hybridized to target mRNA were observed (see Table 2 in Example 1 and Table 5 below). Target sites with hybridized oligonucleotides served as good substrates for RNAse H a resulting in an altered target nucleic acid sequence. As result, the altered target nucleic acid sequence poorly protected the AE during subsequent differential hydrolysis and yielded a low HPA signal. The control reactions demonstrated that the loss of HPA signal depends upon antisense oligonucleotide hybridization and RNAse H.

TABLE 5

| | RLU mRNA: Oligonucleotide | | |
|---|---|---|---|
| | 1:0 | 1:1 | 1:3 |
| − RNASe H | 65324 | 66123 | 65789 |
| + RNAse H | 59456 | 28756 | 24758 |

The oligonucleotide and probe used in Table 5 were AglR72-PS and AE-AglR72-PO

To mimic intracellular conditions and to enhance the ultimate predictive value of the screening assay, hybridization in 2× E. coli RNAse H buffer and physiological buffer were compared. The results for two different oligonucleotides are show in Table 1 using BglR38-PS (SEQ ID NO. 5) (see, Example 1 above) and in Table 6 using AglR72-PS. (SEQ ID NO. 2) The AE-probes had the same nucleotide sequence as the oligonucleotide but were labeled with an AE group and contained phosphodiester linkages. For the oligonucleotides tested, hybridization appeared similar in these two buffer conditions. During the detection step, no competition was observed between the antisense phosphorothioate oligonucleotides and the PO-AE detection probes at 60° C.

TABLE 6

| | RLU mRNA: Oligonuclectide | | |
|---|---|---|---|
| | 1:0 Phy | 1:3 Phy | 1:3 2x |
| − RNAse H | 75938 | 73596 | 71033 |
| + RNAse H | 85205 | 22481 | 20718 |

The specificity and extent of RNAse H digestion of target mRNA was assessed by primer extension analysis. Primer extension analysis was carried out on aliquots from each reaction, that were not contacted with a probe, as described by Kotewicz, et al., Nuc. Acids Res. 16:265 (1988). Globin mRNA (0.25 μg) was hybridized to various concentrations of antisense phosphodiester and phosphorothioate oligonucleotides. Each reaction was adjusted to 1× primer extension buffer (50 mM Tris-HCl, pH 8.3, 75 mM KCl, 3 mM $MgCl_2$, 10 mM DTT) and hybridized to the appropriate extension primer (20-fold molar excess) at 37° C. RNA was extended with 200 U Superscript reverse transcriptase (BRL) in the presence of $^{32}p$ dCTP for one hour at 37° C. and analyzed by polyacrylamide gel electrophoresis (PAGE).

Generation of the complete 201 base extension product from the BglR179 primer was observed in samples lacking BglR38 oligonucleotide or containing BglR38 oligonucleotide but lacking RNAse H. Extension of RNAse H digested target mRNA treated with both phosphodiester and phosphorothioate versions of BglR38 indicated nearly complete specific digestion at oligonucleotide:target ratios of 1:1 and 5:1. Little or no full length product (201 bases) and a strong 140 base extended product generated from extension of RNAse H-digested target were observed.

In experiments using 2× E. coli RNAse H buffer, BglR38-PS formed the most stable hybrid and the best substrate for RNAse H digestion, while other oligonucleotides, most notably AglR72-PS, performed relatively poorly. These results agreed with previously obtained hybridization data. BglR38-PS performed well in the assay at both the 1:1 ratio and the 1:3 ratio with an average 35-fold drop in HPA signal. In contrast, AglR72-PS performed poorly at both ratios with only a 2- to 3-fold drop in signal.

Determination of hybridization kinetics

The kinetics of BglR38-PS (SEQ ID NO. 5) and AglR72-PS (SEQ ID NO. 2) hybridization to mRNA were measured to further evaluate hybridization of these oligonucleotide to their target nucleic acid sequences. Oligonucleotides were hybridized as described above, and 15 μL aliquots were removed at 0, 10, 20, 30, 60, 90, and 120 minute time points and placed on ice. All reactions were divided into standard (+) and (−) RNAse H digestion reactions. The (+) reactions were treated with a high concentration of RNAse H (1.5 units) for 20 minutes to minimize oligonucleotide cycling (i.e., release of the oligonucleotide following digestion of the target and subsequent hybridization to another target molecule). RNAse H digestion was stopped by heating at 95° C. for 5 minutes. Standard HPA analysis was then conducted as described above.

The hybridization kinetics of BglR38-PS and AglR72-PS were compared. Hybridization of BglR38-PS to its target was nearly complete in 10 minutes, whereas AglR72-PS hybridized slowly and incompletely to its target over the 2 hour hybridization reaction. These results corroborated the hybridization characterization data for these oligonucleotides as described above, and indicated that the described assay measures oligonucleotide hybridization. Non-target-region positive HPA controls showed that signal loss was specifically due to RNAse H-mediated target degradation.

EXAMPLE 5

This example describes an assay for measuring the activity of a RNAse A. Substrate for RNAse A was prepared by amplifying template RNA strands using T7 RNA polymerase. Template strands for T7 RNA polymerase were prepared by synthesizing the following two DNA oligonucleotides:

SEQ ID NO. 8 5' AATTTAATACGACTCACTATAGG-GAGAGGTTATCGCTGGATG TGTCTGCGGC 3'; and (2) 5' TCCTGGAATTAGAGGACAAACGGGCAA-CATACCTTGATAATCCAGAAGAA CCAATAA-GAAGATGAGGCATAGCAGCAGGATGAA-GAGGAATATGATAAAACGCCGC AGACACATCCAGCGATAACC 3'

RNA transcripts were produced from these oligonucleotides in a reaction mixture containing the following: 10 μL buffer (40 mM Tris-HCl (pH 8.3), 25 mM NaCl, 12.8 mM $MgCl_2$, 5 mM dithiothreitol, 2 mM spermidine), 0.3 μL oligonucleotide SEQ ID NO. 8 (45 pmoles/μL), 2 μL oligonucleotide SEQ ID NO. 9 (0.5 pmoles/μL), 6.25 μL 40 mM each ATP, CTP, GTP, and UTP, 81.45 μL water, 0.5 μL T7 RNA polymerase (200 units/μL) . The reaction mixtures were incubated at 37° C. for 1 hour.

The amount of transcript yielding about 25–30,000 RLU when hybridized to an AE-labeled probe was determined by mixing different amounts of RNA transcript with an AE-labeled probe and measuring the chemiluminescence using HPA. HPA was performed using 50 μL of the AE-probe (prepared by mixing 50 μL of the stock probe solution with a solution containing 950 μL 2% (w/v) lithium lauryl sulfate, 20 mM EGTA, 20 mM EDTA, 0.1M lithium succinate, 1.1M lithium chloride, pH 4.7). The AE-probe had the following sequence: SEQ ID NO. 10: 5' GAGGCAT-AGCAGCAGGATGAAGAGG 3'. The AE-probe was prepared as described in Nelson et al., supra, containing the AE group between bases 7 and 8. The specific activity of the probe was $2 \times 10^7$ RLU/pmole. The probe stock solution was prepared to a concentration of 1 pmole/mL.

Reactions containing 50 μL of RNA and 50 μL of probe were incubated at 60° C. for 10 minutes. Chemical inactivation of AE was then carried out by adding 300 μL of 0.6M sodium borate, pH 8.5, 1.0% (v/v) Triton X-100 to the reactions, and incubating the reactions at 60° C. for 7 minutes. Reactions were then chilled briefly on ice, and the amount of hybrid-associated acridinium ester label was measured in a Leader luminometer.

The amount of transcript yielding about 25–30,000 RLU corresponded to 3 μL of a 1000× dilution of the reaction. In the subsequent experiments assaying RNAse A, the transcript was used directly from a 100× dilution in STE buffer (0.1M NaCl, 10 mM Tris-HCl (pH 8.0), 1 mM EDTA). The 1000× dilution stopped the T7 polymerase reaction.

The ability of RNAse A to degrade RNA was then measured. Ten-fold serial dilutions in water of a stock solution of RNAse A in water (0.1 units/μL) were prepared immediately before use. Reactions contained the following: 3 μL RNA transcript in STE buffer (1000× dilution of transcript as noted above), 6 μL water, 1 μL RNAse A. Controls contained 1 μL water in place of the RNAse A.

Reactions were incubated at room temperature for 1 hour, diluted by the addition of 40 μL water, and then denatured by heating at 95° C. for 5 minutes. Reactions were then chilled on ice for 1 minute. The amount of RNA transcript remaining was determined using 50 μL of stock AE-probe as described above. Results are shown in Table 7.

TABLE 7

| Reaction Condition | RLU |
|---|---|
| No RNAse A | 28,173 |
| No RNAse A | 25,040 |
| RNAse A, $10^{-8}$ units | 24,900 |
| RNAse A, $10^{-7}$ units | 29,007 |
| RNAse A, $10^{-6}$ units | 27,849 |
| RNAse A, $10^{-5}$ units | 11,766 |
| RNAse A, $10^{-4}$ units | 1,946 |
| RNAse A, $10^{-3}$ units | 993 |
| No Target | 950 |

The control without RNAse A was run in duplicate. The "No target" reaction lacked the RNA transcript. The assay was able to detect Between $10^{-5}$ to $10^{-6}$ units of RNAse A.

Other embodiments are within the following claims.

We claim:

1. A method of assaying the ability of an oligonucleotide to form a hybrid with a target nucleic acid sequence comprising the steps of:
   a) contacting a test sample containing said target nucleic acid sequence with said oligonucleotide;
   b) treating said test sample containing said target nucleic acid sequence and said oligonucleotide with an agent which cuts, degrades or chemically alters duplex nucleic acids;
   c) contacting the treated test sample with a labeled probe under stringent hybridization conditions, wherein said probe can hybridize to a non-altered target nucleic acid sequence such that the probe label is protected from subsequent chemical inactivation but said probe cannot hybridize to an altered target nucleic acid sequence leaving said probe label unprotected from subsequent chemical inactivation;
   d) treating the probe-contacted test sample with an agent which inactivates said unprotected probe label in said sample; and
   e) measuring the hybridization of said probe to said non-altered target nucleic acid sequence by measuring the amount of protected probe label.

2. The method of claim 1, wherein said measuring of said hybridization is done in a homogenous assay without physically separating hybridized from non-hybridized probe.

3. The method of claim 2, wherein said target nucleic acid is RNA and said oligonucleotide is DNA or modified DNA.

4. The method of claim 3, wherein said probe label comprises an acridinium ester group.

5. The method of claim 4, wherein said contacting a test sample is carried out under physiological conditions.

6. The method of claim 4, wherein said oligonucleotide comprises one or more phosphorothioate linkages.

7. The method of claim 4, further comprising the step of degrading said oligonucleotide present in said treated sample with DNase after said step b) and prior to said step c).

8. The method of any one of claims 1–7, wherein said duplex-altering agent is RNAse H.

9. A method of assaying the ability of an oligonucleotide to form a hybrid with a target nucleic acid sequence comprising the steps of:
   a) contacting a test sample containing said target nucleic acid sequence with said oligonucleotide;
   b) dividing said test sample containing said target nucleic acid sequence and said oligonucleotide into a treated sample and a control sample;
   c) contacting the treated test sample with an agent which cuts, degrades, or chemically alters duplex nucleic acids;
   d) contacting said treated test sample and said control sample with a labeled probe under stringent hybridization conditions, wherein said probe can hybridize to non-altered target nucleic acid sequence such that the probe label is protected from subsequent chemical inactivation but said probe cannot hybridize to altered target nucleic acid sequence leaving said probe label unprotected from subsequent chemical inactivation;

e) treating the probe-contacted test sample with an agent which inactivates said unprotected label in said sample; and f) measuring the hybridization of said probe to non-altered target nucleic acid in said control sample and said treated test sample by measuring the amount of protected probe label.

10. The method of claim 9, wherein said measuring of said hybridization is done in a homogenous assay without physically separating hybridized from non-hybridized probe.

11. The method of claim 10, wherein said target nucleic acid sequence is RNA and said oligonucleotide is DNA or modified DNA.

12. The method of claim 11, wherein said probe comprises an acridinium ester group.

13. The method of claim 12, wherein said contacting a test sample is carried out under physiological conditions.

14. The method of claim 12, wherein said oligonucleotide comprises one or more phosphorothioate linkage.

15. The method of any one of claims 9–14 wherein said duplex-altering agent is RNAse H.

16. A method of assaying the ability of a ribozyme to cleave a target nucleic acid sequence comprising:

a) contacting a sample containing said target nucleic acid sequence with a ribozyme;

b) contacting said sample containing said target nucleic acid sequence and said ribozyme with a labeled probe under stringent hybridization conditions, wherein said probe can hybridize to non-altered target nucleic acid sequence such that the probe label is protected from subsequent chemical inactivation but said probe cannot hybridize to altered target nucleic acid sequence leaving said probe label unprotected from subsequent chemical inactivation;

c) treating the probe-contacted test sample with an agent which inactivates said unprotected probe label in said sample; and d) measuring the hybridization of said probe to non-altered target nucleic acid by measuring the amount of protected probe label.

17. The method of claim 16, wherein said measuring of said hybridization is done in a homogenous assay without physically separating hybridized from non-hybridized probe.

18. The method of claim 17, wherein said probe comprises an acridinium ester label.

19. The method of claim 18, wherein said contacting a test sample is carried out under physiological conditions.

20. A homogenous method of assaying the ability of a first agent to alter a target nucleic acid comprising the steps of:

a) contacting a test sample containing said target nucleic acid with said first agent to form a treated test sample;

b) contacting the treated test sample with a labeled probe under stringent hybridization conditions, wherein said probe can hybridize to a non-altered target nucleic acid sequence such that the probe label is protected from subsequent chemical inactivation but said probe cannot hybridize to an altered target nucleic acid sequence leaving said probe label unprotected from subsequent chemical inactivation;

c) treating the probe-contacted test sample with a second agent which inactivates said unprotected probe label in said sample; and d) measuring the hybridization of said probe to non-altered target nucleic acid by measuring the amount of protected probe label.

21. The method of claim 20, wherein said probe comprises an acridinium ester.

22. The method of claim 21, wherein said first agent is either a nuclease or a restriction enzyme.

23. A kit for measuring the hybridization of an oligonucleotide to a target nucleic acid sequence comprising:

a) an agent which will cut, degrade, or chemically alter duplex nucleic acids in a region comprising said target nucleic acid sequence and an oligonucleotide perfectly complementary thereto in said region, and b) a probe comprising an acridinium ester labeled oligonucleotide sequence which will hybridize to said target nucleic acid sequence and is not capable of being cut, degraded, or chemically altered by said agent.

24. The kit of claim 23, wherein said target nucleic acid sequence is RNA.

25. The kit of claim 24 wherein said agent is RNAse H.

26. The kit of claim 24 wherein said agent is a ribozyme.

27. The kit of claim 23 wherein said agent and said probe are in separate containers within said kit.

28. A kit for measuring the hybridization of an oligonucleotide to a target RNA nucleotide base sequence comprising:

a) an agent which will cut, degrade, or chemically alter duplex nucleic acids in a region of said target RNA comprising said RNA and an oligonucleotide perfectly complementary thereto in said region, wherein said agent is either a ribozyme or an enzyme with RNAse H activity, and b) a probe comprising an acridinium ester labeled oligonucleotide sequence which will hybridize to said target RNA and is not capable of being cut, degraded, or chemically altered by said agent.

29. The kit of claim 28, wherein said agent is RNAse H.

30. The kit of claim 28 wherein said agent is a ribozyme.

31. The kit of claim 28 wherein said agent and said probe are in separate containers within said kit.

* * * * *